US00PP08356P

United States Patent [19]

Tracy, Sr.

[11] Patent Number: Plant 8,356

[45] Date of Patent: Aug. 31, 1993

[54] HYBRID TEA ROSE PLANT NAMED HILRAP

[75] Inventor: Daniel L. Tracy, Sr., Richmond, Ind.

[73] Assignee: E. G. Hill Company, Inc., Richmond, Ind.

[21] Appl. No.: 919,721

[22] Filed: Jul. 24, 1992

[51] Int. Cl.[5] ..... A01H 5/00

[52] U.S. Cl. ..... Plt./21

[58] Field of Search ..... Plt./20, 21

*Primary Examiner*—Howard J. Locker

*Attorney, Agent, or Firm*—Christie, Parker & Hale

[57] ABSTRACT

A new variety of hybrid tea rose having rich velvety red flowers produced on a plant suitable for greenhouse growing.

2 Drawing Sheets

SUMMARY OF THE INVENTION

The present invention relates to a new and distinct variety of rose plant of the hybrid tea rose class, which was originated by my crossing as the seed and pollen parents two unnamed and unpatented seedlings of my creation. The varietal denomination of this new rose is 'Hilrap'.

Among the novel characteristics possessed by this new variety which distinguishes it from all other varieties of which I am aware are its attractive rich velvety red flowers with excellent imbrication. As a partially opened cut flower 'Hilrap' is urn shaped with an attractive elongated bud. The flowers are large and are borne singly in a manner typical of hybrid tea varieties.

Asexual reproduction by grafting of the new variety as performed in Richmond, Ind. shows that the foregoing and other distinguishing characteristics come true to form and are established and transmitted through succeeding propagations. The new variety can be asexually propagated by budding, grafting, propagation from cuttings and by micropropagation.

BRIEF DESCRIPTION OF ILLUSTRATION

The accompanying illustrations show typical specimens of the flowers and vegetative growth of the new variety depicted in color as nearly true as it is reasonably possible to make the same in a color illustrations of this character. Phenotypic expression, including colors, may vary depending upon growing conditions, such as different climate, soil, and cultivation conditions.

One of the illustrations shows plant parts, including compound five and seven leaflets, a stem, new growth, buds after sepals part and after sepals fall, a bloom ⅓ open and a bloom fully open. The other illustration depicts typical form and configuration of flower and bud as cut flowers.

DETAILED DESCRIPTION OF THE NEW VARIETY

The following is a detailed description of my new variety, with color terminology in accordance with The Royal Horticultural Society Colour Chart (R.H.S.C.C.). The terminology used in the color descriptions herein refers to plate numbers in the aforementioned color chart.

Parentage: Seedling.

*Seed parent.*—Unnamed seedling.

*Pollen parent.*—Unnamed seedling.

Class: Hybrid tea.

The following further horticultural observations were made of specimens grown in a greenhouse in Richmond, Ind. in the months of November and February.

FLOWER

Blooming habit: Nearly continuous.

A. Bud:

(1) *Size.*—Very large.

(2) *Form.*—Ovoid, becoming urn shaped as sepals fall.

(3) *Color.*—When sepals first divide, near 59A.

(4) *Sepals.*—Simple to slightly foliated. Size: About ¼-178 inches. Color: Near 143C.

(5) *Peduncle.*—Length — about 4 inches. Aspect — smooth. Strength — slender. Color — near 144B.

B. Bloom:

(1) *Size.*—Average size when fully expanded — about 4½ inches.

(2) *Borne.*—Singly.

(3) *Form.*—Very high-centered, holds its' high center well; outer petals reflex and quill to points, inner petals roll under.

(4) *Petalage.*—Number of petals — usually about 30–35.

(5) *Color.*—After sepals fall and petals unfurl, outer petals top surface, near 53A, petal undersurface near 46A. Inner petals top surface near 46A and inner petals undersurface near 60B. General tonality from a distance is attractive rich clear medium red. Color at point of petal attachment is near 158A. As blooms age, outer petals red coloration darkens somewhat to near 45B (petal top surface) and near 46C (petal undersurface) and holds coloration to open bloom.

C. Petals:

(1) *Texture.*—Leathery and thick.

(2) *Appearance.*—Inside rich velvety, outside satiny.

(3) *Form.*—Urn-shaped.

(4) *Arrangement.*—Imbricated.

(5) *Petaloids in center.*—Many.

(6) *Persistence.*—Persistant.

(7) *Fragrance.*—Very slight.

(8) *Lasting quality.*—Very long lasting on plant and long lasting after cutting.

REPRODUCTIVE ORGANS

A. Stamens, filaments and anthers:
*Arrangement and color.*—Regularly arranged around styles. Color — filaments near 45C, anthers near 10C.

B. Pollen:
*Color.*—Near 158A.

C. Styles: Bunched in uneven lengths and thin.

D. Stigmas: Near 158A.

E. Hips:
*Shape.*—Obovate.
*Size.*—Small.
*Color.*—Near 25A.

PLANT

A. Form: Bushy, upright.

B. Growth: Very vigorous.

C. Foliage: Usually compound 3, 5 and 7 leaflets.
(1) *Size.*—Medium.
(2) *Quantity.*—Moderate.
(3) *Color.*—New foliage: Upper side — near 139A. Underside — near 138B. Old foliage: Upper side — near 137A. Underside — near 138B.
(4) *Shape.*—Egg-shaped.
(5) *Texture.*—Upper side is leathery; Underside is smooth.
(6) *Edge.*—Serrated.
(7) *Serration.*—Saw-toothed.

(8) *Leaf stem.*—Color — medium green.
(9) *Petiole color.*—Top surface — near 138A. Undersurface — near 143C.
(10) *Stipules.*—Medium length; substantially parallel; auricle pointing outward and smooth.
(11) *Rachis.*—Upperside is grooved and smooth. Underside with prickles.
(12) *Resistance to disease.*—Moderately susceptible to powdery mildew.

D. Wood:
(1) *New wood.*—Color — near 146B with tones of 184B. Bark — smooth.
(2) *Old wood.*—Color — near 137C. Bark — smooth.
(3) *Flower stem.*—Length from last cut — 22 to 26 inches.

E. Thorns:
*Quantity (main stalk).*—Many, sometimes heavy.
*On laterals from stalk.*—Several.
*Form.*—Thin, angle downwardly and flat base.
*Length.*—Medium.
*Color.*—Near 185A.
*Position.*—Irregular.
*Prickles.*—None.

I claim:

1. A new and distinct variety of rose plant of the hybrid tea rose class, substantially as shown and described.

* * * * *

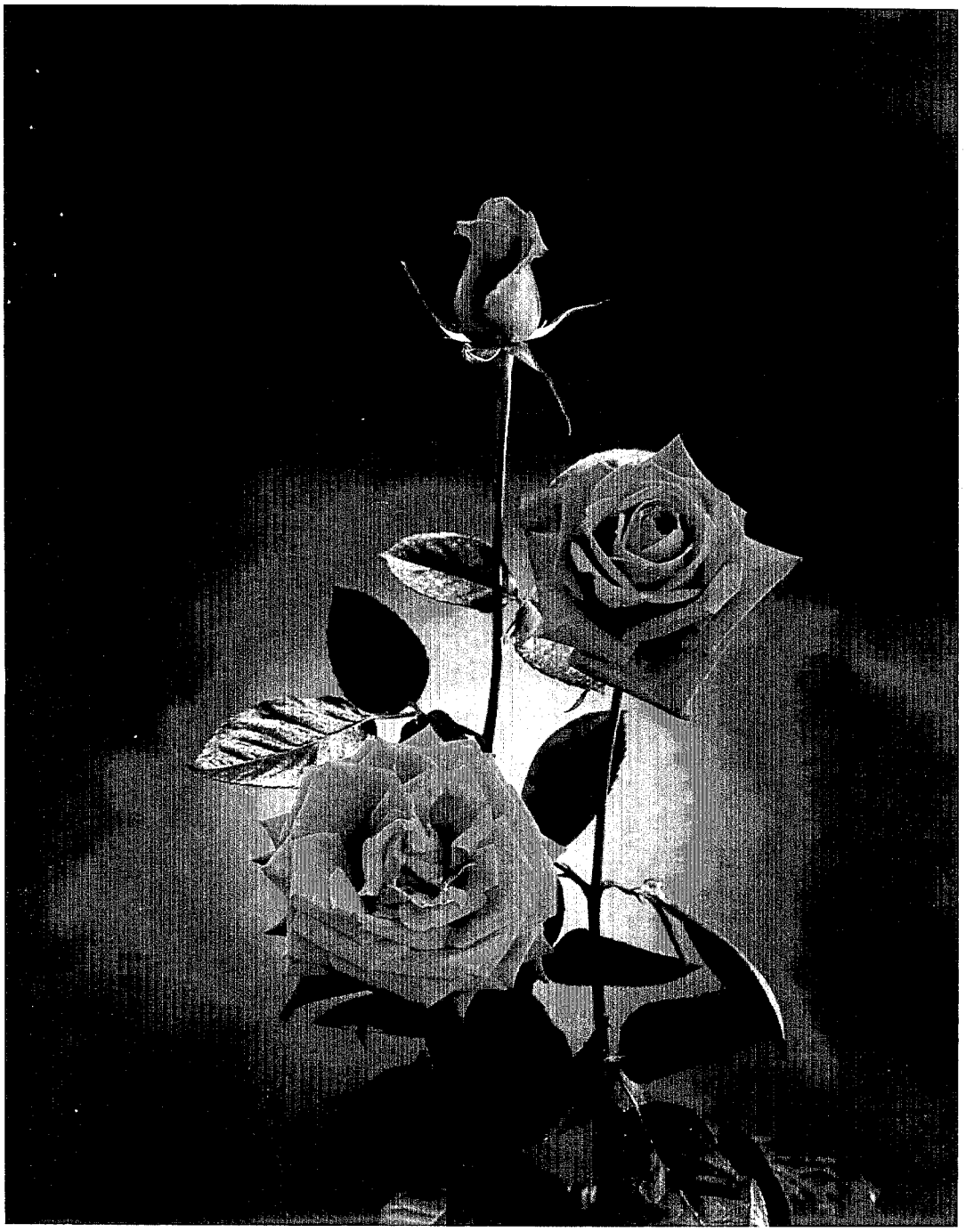

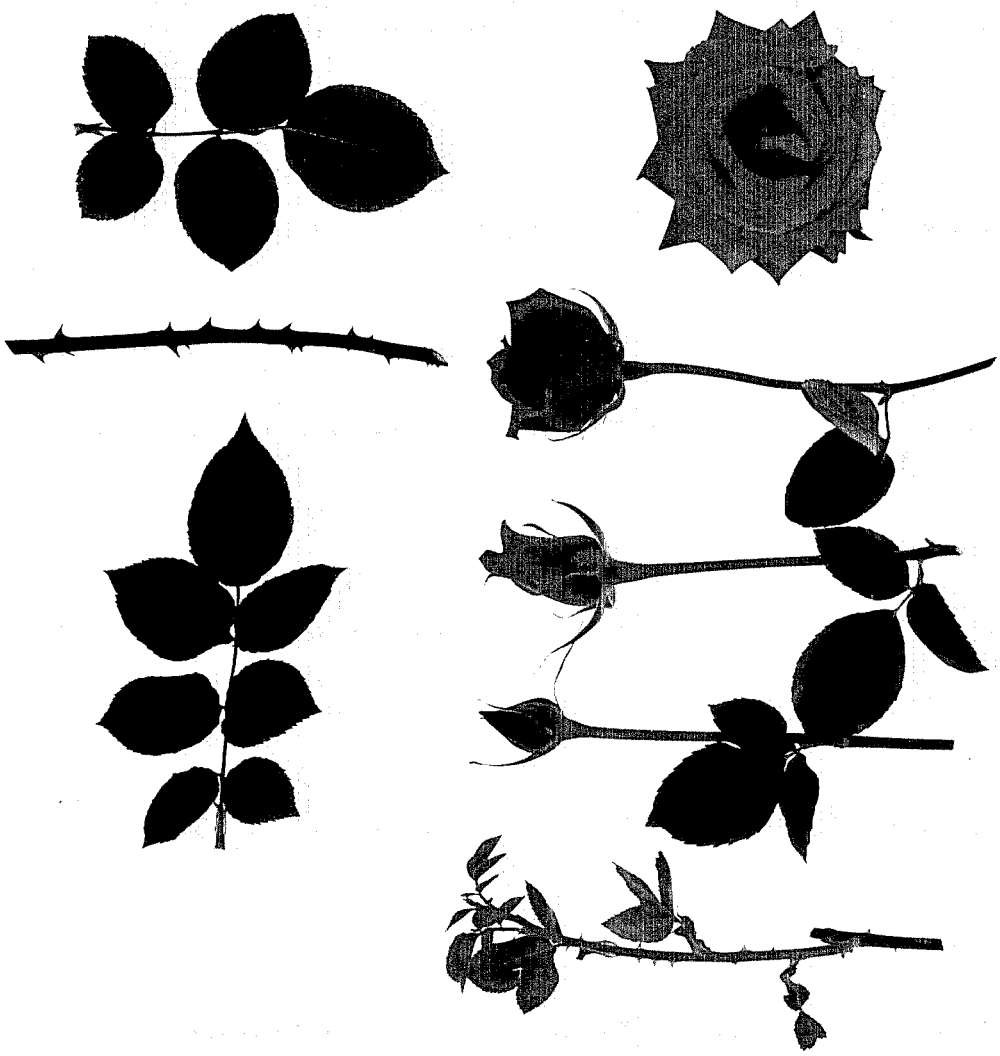

UNITED STATES PATENT AND TRADEMARK OFFICE

CERTIFICATE OF CORRECTION

PATENT NO. : Plant 8,356

DATED : August 31, 1993

INVENTOR(S) : Daniel L. Tracy, Sr.

It is certified that error appears in the above-indentified patent and that said Letters Patent is hereby corrected as shown below:

Column 2, line 17, change "¼-178 inches" to
-- ¼-½ inch --.

Signed and Sealed this

Eleventh Day of October, 1994

*Attest:*

*Attesting Officer*

Bruce Lehman

BRUCE LEHMAN

*Commissioner of Patents and Trademarks*